United States Patent [19]

Pathak et al.

[11] Patent Number: 5,795,296

[45] Date of Patent: *Aug. 18, 1998

[54] PIPELINE PROCESS FOR AUTOMATICALLY MEASURING OBJECT BOUNDARY FROM ULTRASOUND IMAGE SAMPLES

[75] Inventors: Sayan Pathak, Seattle; Vikram Chalana, Mountlake Terrace; Yongmin Kim, Seattle, all of Wash.

[73] Assignee: University of Washington, Seattle, Wash.

[*] Notice: The term of this patent shall not extend beyond the expiration date of Pat. No. 5,605,155.

[21] Appl. No.: 802,979

[22] Filed: Feb. 20, 1997

Related U.S. Application Data

[63] Continuation-in-part of Ser. No. 624,949, Mar. 29, 1996, Pat. No. 5,605,155.

[51] Int. Cl.$^6$ .......................................................... A60B 8/00
[52] U.S. Cl. ................................................ 600/443; 600/449
[58] Field of Search ................... 128/660.01, 660.07, 128/660.09, 661.03, 661.09, 661.1, 382

[56] References Cited

U.S. PATENT DOCUMENTS

| | | |
|---|---|---|
| 5,107,838 | 4/1992 | Yamaguchi . |
| 5,360,006 | 11/1994 | Geiser et al. . |
| 5,457,754 | 10/1995 | Han et al. . |
| 5,465,721 | 11/1995 | Kishimoto et al. . |
| 5,469,950 | 11/1995 | Iizuka et al. . |
| 5,492,125 | 2/1996 | Kim et al. . |
| 5,588,435 | 12/1996 | Weng et al. ................ 128/660.07 |
| 5,605,155 | 2/1997 | Chalova et al. ............. 128/660.07 |
| 5,655,535 | 8/1997 | Freimel et al. .............. 128/660.07 |

OTHER PUBLICATIONS

"Deformable Models for Boundary Detection on Ultrasound Images," Univ. of Washington, Apr. 10, 1995.

Chalana et al., "A Multiple Active Contour Model for Cardiac Boundary Detection on Ethocardiographic Sequences," IEEE Transcactions on Medical Imaging, vol. 15, No. 3 Jun. 1996.

Chalana et al., "Automati Fetal Head Measurements from Sonographic Images," Acad. Radiol. 1996; 3:628–635.

Lee et al., "Mediastation 5000: An Integrated Multimedia Video and Audio Processing System".

Kass et al., "Snakes: Active Contour Models;" International Journal of Computer Vision; 1988.

Geiser et al., "A Second–Generation Computer–Based Edge Detection Algorithm for Short–Axis, Two–Dimensional Echocardiographic Images: Accuracy and Improvement in Interobserver Variability;" vol. 3, No. 2 Mar–Apr. 1990.

Thomas et al., "Automatic Segmentation of Ultrasound Images Using Morphological Operators;" IEEE Transactions on Medical Imaging, vol. 10, #2; Jun. 1991.

Matsopoulos et al., "Use of Morphological Image Processing Techniques for the Measurement of Fetal Head from Ultrasound Images;" Pattern Recognition, vol. 27, No. 10; 1994.

Cohen, Laurent D.; "Note: On Active Contour Models and Ballons;" CVGIP: Image Understanding, vol. 53, No. 2; Mar. pp. 211–218; 1991.

*Primary Examiner*—Francis Jaworski
*Attorney, Agent, or Firm*—Steven P. Koda

[57] ABSTRACT

An ultrasound system automatically measures fetal head size from ultrasound images. An ultrasound image of the fetal head is detected. A radial maxima point is identified on each of a plurality of radii extending from a substantially common vertex point within the fetal head image. Each radial maxima point corresponds to an ultrasound sample along its corresponding radius, and has a maximum ultrasound echo strength. Outlier points are removed and the curve filtered to derive an initial fetal head boundary. An inner fetal head boundary and outer fetal head boundary are derived from the initial fetal head boundary and a predetermined fetal skull thickness, and fetal head size is computed from the inner fetal head boundary and the outer fetal head boundary. Processing is allocated among multiprocessors and performed in pipeline fashion to enable real-time interactive imaging and measuring.

14 Claims, 11 Drawing Sheets

PIPELINE PROCESS FOR AUTOMATICALLY MEASURING OBJECT BOUNDARY FROM ULTRASOUND IMAGE SAMPLES

CROSS REFERENCE TO RELATED APPLICATION

This is a continuation in part of U.S. Pat. No. 5,605,155 issued Feb. 25, 1997 for Ultrasound System for Automatically Measuring Fetal Head Size (Ser. No. 08/624,949 filed Mar. 29, 1996).

BACKGROUND OF THE INVENTION

This invention relates to image processing methods used in ultrasound medical diagnostic imaging systems. More particularly, this invention relates to a method for automatically measuring an object boundary from ultrasound image data.

Ultrasound medical diagnostic systems generate images of anatomical structures within a patient's body by scanning a target area with ultrasound signals. Typically, ultrasound signals on the order of 2.0 MHz to 10 MHz are transmitted into a patient via a transducer probe. The transmitted ultrasound energy is in part absorbed, dispersed, refracted, and reflected by the patient's body. Reflected ultrasound energy is received at the transducer probe where it is converted into electronic echo signals. The echo signals undergo beam-forming to correlate the ultrasound signals. Subsequently the beam-formed signals are processed to analyze echo, doppler, and flow information and to obtain an image of the patient's targeted anatomy (e.g., tissue, fetus, vessels).

A B-mode image, for example, is a brightness image in which component pixels are brightened in proportion to a corresponding echo signal strength. The brightness image represents a cross section of a patient target area through a transducer's scanning plane. Typically the B-mode image is a gray scale image in which the range of darker to lighter gray-scale shades corresponds to increasing brightness or echo strength.

One common ultrasound application is to view a fetus within the mother's womb during a prenatal care stage. It is desirable to view the fetus to diagnose its health, sex, and age. Fetal head measurements, a subject of this invention, are useful for evaluating fetal growth, estimating fetal weight, predicting intra-uterine growth retardation and fetal maturity, and estimating gestational age. The fetal head measurements of interest include fetal head circumference ("HC") and fetal biparietal diameter ("BPD"). The biparietal diameter is the distance between the two parietal bones of the skull at points just above the ears.

Conventionally, these measurements have been performed manually by a sonographer. Head circumference is measured by plotting minor and major ellipse axes on the image, then calculating circumference based upon such axial distances. Thus, the fetal head is assumed to be an ellipse. The ellipse circumference serves as an estimate of the fetal head circumference. Biparietal diameter is measured using a caliper to read the distance on the fetal ultrasound image. One shortcoming of this conventional manual measurement approach is that the time used in performing the measurements is a large portion of the overall fetal ultrasound scanning process time. Another shortcoming is that the manual measurements introduce operator inaccuracies which impact related and subsequent diagnoses. Some efforts to reduce the time requirement have added to the inaccuracies.

For example, by opening an ellipse to estimate head circumference an inaccuracy is introduced. Specifically, because the head is not likely to be a perfect ellipse, the circumference has a degree of inaccuracy. Because the head circumference is used to derive other parameters and values, there is a degree of inaccuracy throughout the diagnostic evaluation. Even more problematic is that the inaccuracy is not consistent. Different operators may introduce different degrees of inaccuracy. Thus, it is difficult to obtain a meaningful profile of statistics for a given population of data. For example, growth curves used for aging the fetus have been derived from data having varying degrees of inaccuracies decreasing the reliability of the diagnosed age. Reliability of other estimates such as computation of head-to-abdominal circumference ratios and estimation of fetal weight also is reduced. An error in estimating biparietal diameter by about 0.8 mm, for example, changes estimated gestational age by about one-half week. An error in estimating head circumference by about 7 mm changes estimated gestational age by about one full week. Variability of fetal head size measurements among different operators often ranges between 2% and 7%. As a result, estimated gestational age derived from manual measurements of different sonographers have varied by more than one week. Accordingly, there is a need for a more accurate, more consistent method for measuring fetal head size.

SUMMARY OF THE INVENTION

According to the invention, an object boundary such as fetal head size, as displayed in an ultrasound medical diagnostic imaging system, is automatically measured. An operator positions an ultrasound transducer probe on a mother's abdomen to display the fetus within the womb. The operator manipulates the probe to image the fetal head or another object at a desired orientation. Specifically, the probe is oriented to capture a cross-section of the fetal head along a longitudinal axis (e.g., from the top of the head downward.) The cross-section is captured as a snap-shot and displayed as a two dimensional ("2D") ultrasound image. The operator then sets a marker at the approximate center of the fetal head. The fetal head boundary and fetal head size then are automatically derived from the ultrasound data and the marked position.

According to one aspect of the invention, the measuring calculation is performed automatically for multiple frames of image data. An operator selects an initial market point which is used for subsequent frames of data. One advantage of the invention is that the operator is able to move the transducer probe during the process. Measurements are derived in real time and displayed. The operator is able to view the display and determine that a desirable image plane is shown. The operator then triggers the measurements to be recorded for such image plane. Thus, measurements are continually derived and displayed in real time for multiple image frames, even as the probe moves. In addition the operator presses a button to record measurements for select image frames. The operator uses the measurements for a select image frame as the final measurements for the fetal head measurement. In one embodiment, the system uses criteria (e.g., largest derived measurements) to select a measurement from among the measurements for multiple frames. Unless overridden by the operator such select measurement is used as the final fetal head measurement.

According to another aspect of the invention, the measuring process is performed in a stand-alone mode or in a pipeline mode. In stand-alone mode a snapshot of ultrasound image data is captured and used to display a 2D ultrasound image. The operator selects a point within the fetal head boundary appearing in the image. The system then determines the fetal head boundaries and derives the fetal head measurements. In the pipeline mode, the operator positions the probe to obtain a desired view of the fetal head. While ultrasound data continues to be gathered, the operator selects a point within the fetal head boundary appearing on the display screen. Such point is used to derive the fetal head boundary for the current and subsequent frames of ultrasound image data. The operator can save snapshots of the image and corresponding measurements. The operator also can move the ultrasound probe to obtain different viewing angles of the fetal head. The operator is thus able to see the measurements on the display as the probe is moved. An advantage of such interactive capability is that the operator can identify the image where the maximum measurement value is determined and save such measurement as the most accurate fetal head size measurement.

According to another aspect of the invention, at one step radial samples of a filtered gradient of the image are taken to define radial maxima points. Such radial samples are based from the operator selected marker point extending outward to a brightened maxima point (i.e., strongest endpoint of the radial line). Such maxima points are expected to represent a crude boundary of the fetal skull. According to one embodiment more than 100 radial samples are taken to define the radial maxima points. Because some points along the true fetal skull may not have been captured during the ultrasound scan, some of the radial maxima points may occur at an exaggerated radial increment beyond the true fetal skull. These are referred to herein as outlier points. At a next step, a statistical filter is used to filter away the outlier points. In one embodiment all boundary points with a radial distance greater than two standard deviations from a mean are automatically removed. The filtered crude boundary is the initial boundary estimate of the fetal head.

According to another aspect of the invention, the initial boundary is contracted, then processed using an active contour model to derive an inner boundary for the fetal skull. The contouring process is an iterative process of fitting the initial boundary and ultrasound data to a contour model. The result is the inner boundary estimate.

According to another aspect of the invention, at another step the outer boundary of the fetal skull is derived from the inner boundary. The inner boundary is expanded by an expansion factor. The expanded curve then is processed using the active contour model to find the outer boundary.

According to another aspect of the invention, at another step fetal head size is automatically computed from the inner and outer boundaries of the fetal head. Fetal head circumference is measured by automatically fitting an ellipse to the outer boundary, then calculating the circumference of such ellipse. Biparietal diameter is measured by fitting an ellipse to each of the outer and inner boundaries, then calculating the average length of the inner ellipse's minor axis and the outer ellipse's minor axis.

According to another aspect of the invention, the image processing is allocated among multiprocessors to improve execution time. A first multiprocessor is allocated the tasks of inputting a frame of image data and processing the image data to obtain image force values. A second multiprocessor uses the image data and image force values to apply the active contour model and derive the inner and outer boundaries. For a given frame of image data, one multiprocessor receives the image data, stores the received data in one bank of shared memory, generates image forces, $f_x$ and $f_y$, for the received image data, and copies the image data and image forces for the received frame into another bank of the shared memory. Concurrently, the other multiprocessor processes the image data from a preceding frame of image data to generate the initial curve, the inner and outer boundary, and the head measurements for such prior frame of image data. In addition such other multiprocessor outputs the image data for such prior frame and the inner and outer boundaries and the head measurements derived from the image data for such prior frame to an output buffer.

According to one advantage of the invention, the automatic measuring process reduces the portion of diagnostic scanning time allocated for measuring fetal head size. According to another advantage of the invention, the automatic measuring process reduces interoperator measurement deviations, thereby improving the reliability of such measurements as health and diagnostic indicators. The invention will be better understood by reference to the following detailed description taken in conjunction with the accompanying drawings.

DESCRIPTION OF SPECIFIC EMBODIMENTS

Exemplary Host Platform

Figure 1:
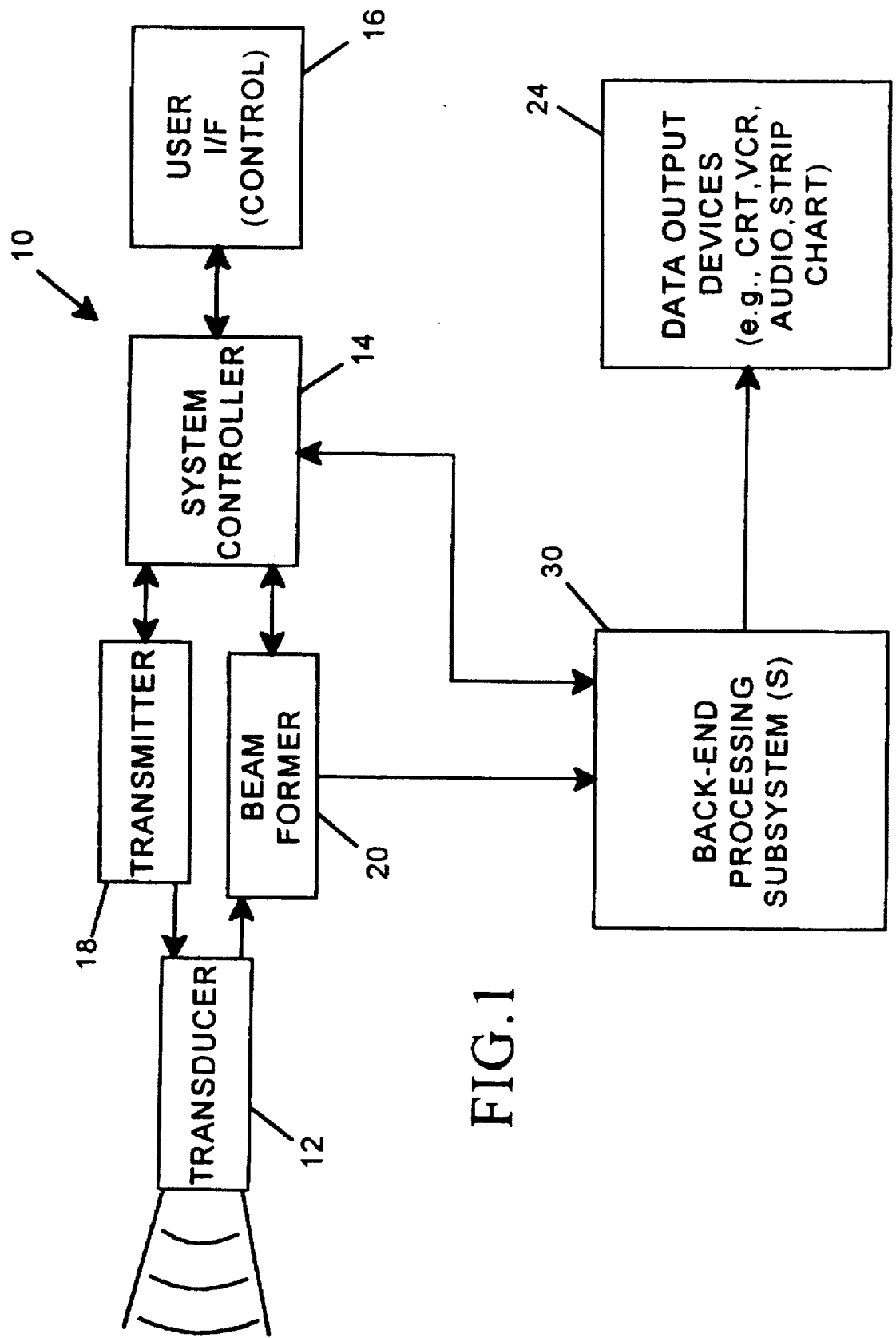
FIG. 1 is a block diagram of an ultrasound medical diagnostic imaging system.

FIG. 1 shows a block diagram of a host ultrasound medical diagnostic imaging system 10 for implementing a method embodiment of this invention. The function of the system 10 is to perform diagnostic imaging of a patient using ultrasound data. Ultrasound signals are transmitted via transducer 12 into a patient. In the case of a fetal ultrasound scan, the ultrasound signals are transmitted into the fetus. Reflected signals are detected and used to derive internal images of the patient, or fetus, for a scanned area/volume, such as a fetal head.

A system controller 14 receives and displays user control information via a user interface 16. During operation, system control signals are output to an ultrasound front end (i.e., transducer 12, a transmitter 18, a beam-former 20, and related circuitry) and to various subsystems. Transmitter 18 generates output signals to transducer 12 to define aperture, apodization, focus, and steering of ultrasound signals. Transducer 12 is an array of transducer elements. The elements define multiple channels, each channel for transmitting and/or receiving ultrasound signals. Transmitted ultrasound signals are in part absorbed, dispersed, refracted, and reflected when travelling through a patient or fetus. Reflected signals are sensed by transducer 12 and captured as a patterned beam by beam-former 20. The captured signals are sent to one or more back-end processing subsystems 30. The function of the back-end processing subsystem(s) 30 is to process the raw beam data and generate image data for output devices 24.

Figure 2:
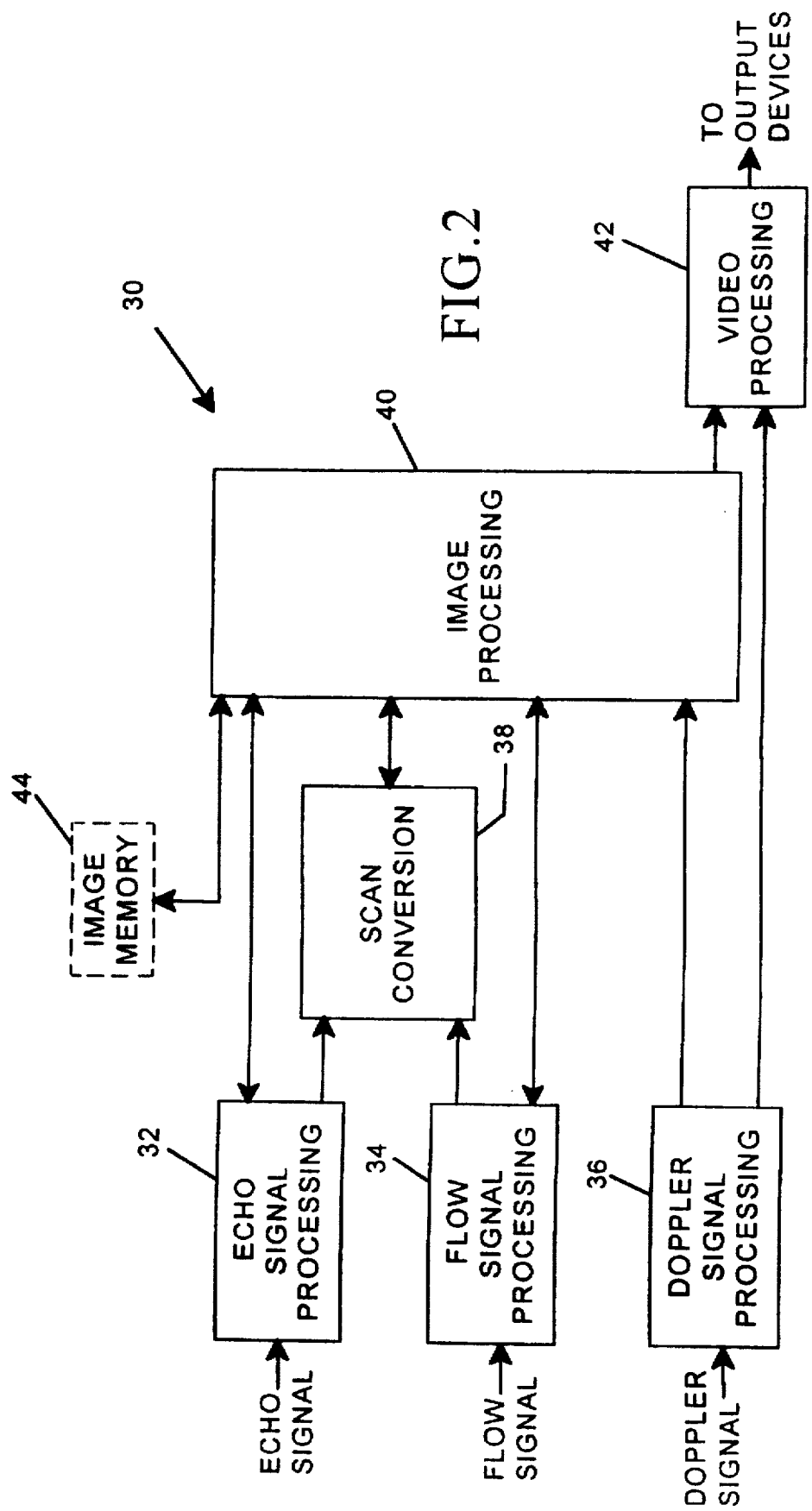
FIG. 2 is a control flow diagram of back-end processing tasks.

FIG. 2 is a block diagram of back-end processing tasks 32-40. Digital echo signals, flow signals, and/or doppler signals are received at the back-end processing subsystem(s) 30 according to various modes of operation. In one embodiment there is a hard-wired subsystem for each of the back-end processing tasks 32-40. In another embodiment there are one or more processor boards respectively programmed to perform one or more of the tasks 32-40. In a preferred embodiment the back-end processing subsystem (s) 30 are implemented with at least one programmable processor board to perform one or more tasks 32-40, and 0 or more dedicated boards to perform, respectively, 0 or more of the remaining tasks 32-40.

The input signals received at the back-end subsystem(s) 30 are referred to herein as vector signals. For a transducer 12 performing sector scanning, the vector signals are digital polar-coordinate data samples of echo, flow, and/or doppler signals. For a transducer 12 performing linear scanning, the vector signals are digital cartesian-coordinate data samples of echo, flow, and/or doppler signals.

The back-end processing tasks include echo signal processing 32, flow signal processing 34, doppler signal processing 36, scan conversion 38, image processing 40, and video processing 42. Echo signal processing 32 typically encompasses signal enhancement filtering, energy detection, and image enhancement filtering. Various filtering and convolution techniques are employed. The purpose of echo signal processing 32 is to enhance the signal-to-noise ratio of the echo signal. Flow signal processing 34 analyzes signals for flow parameters. Typical parameter derivations include sample correlation and flow averaging. The purpose of flow signal processing 34 is to identify flow and turbulence within a scanned area. Doppler signal processing 36 typically encompasses signal enhancement filtering, spectral estimation processing, energy detection, and derived waveform filtering. The purpose of doppler signal processing 36 is to identify and filter out doppler shift, to improve spectral frequency response and to coordinate spectral mapping.

A scan conversion process 38 converts the processed vector data streams from echo signal processing 32 and flow signal processing 34. For polar-coordinate vector data, the data is converted into cartesian-coordinate raster data. For cartesian-coordinate vector data, the data is scaled into cartesian-coordinate raster data.

Image processing 40 includes image enhancement and processing executed on the raster data or vector data. In an off-line delayed playback (e.g., cine playback) mode of operation image data, vector data and/or raster data is received from image memory 44 and processed. Preferably, image processing 40 performs image processing functions on the ultrasound images by applying the active contour model, as will be discussed in detail below. However, as will be appreciated, it is not necessary that image processing functions for applying the active contour model be performed within a resident subsystem 30.

For example, an external image signal processor may perform some or all of the image processing task 40. Image signal processors are well known in the art, and any one of a number of known processors may be acceptable. An example of an acceptable signal processor is a Sun Sparcstation 20 workstation (Sun Microsystems, Mountain View, Calif.).

Video processing 42 executes on the image processed data to generate video signals, audio signals, and graphing signals for output to a display device, audio device, storage device (e.g., VCR), and/or charting device. Video processing 42 in some applications also executes on doppler processed vector data to generate similar video signals, audio signals, and graphing signals for output to the display device, audio device, storage device, and/or charting device.

Figure 3:
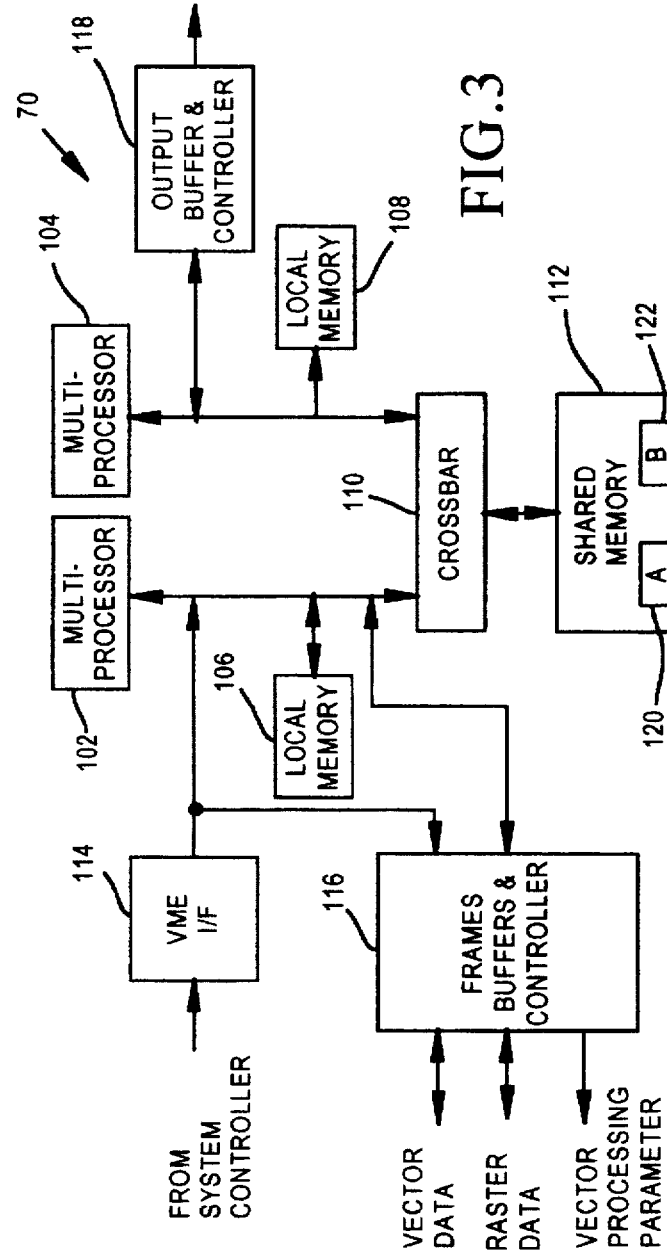
FIG. 3 is a block diagram of a programmable ultrasound signal processing apparatus for implementing the method of this invention.

FIG. 3 is a block diagram of a programmable processor subsystem 70 for implementing one or more of the tasks 32-40. In a preferred embodiment subsystem 70 embodies or is part of the back-end subsystems 30. In another embodiment subsystem 70 is an external processing subsystem receiving data from a subsystem 30 or other part of the system 10. Apparatus 70 includes multiple processors for performing the various vector processing, image processing, scan conversion and/or video processing tasks. In a specific embodiment a pair of processors 102, 104 are included. The apparatus 70 also includes local memory 106, 108, crossbar switch 110, shared memory 112, interface 114, frame buffer/ controller 116 and output buffer/controller 118.

Figure 4:
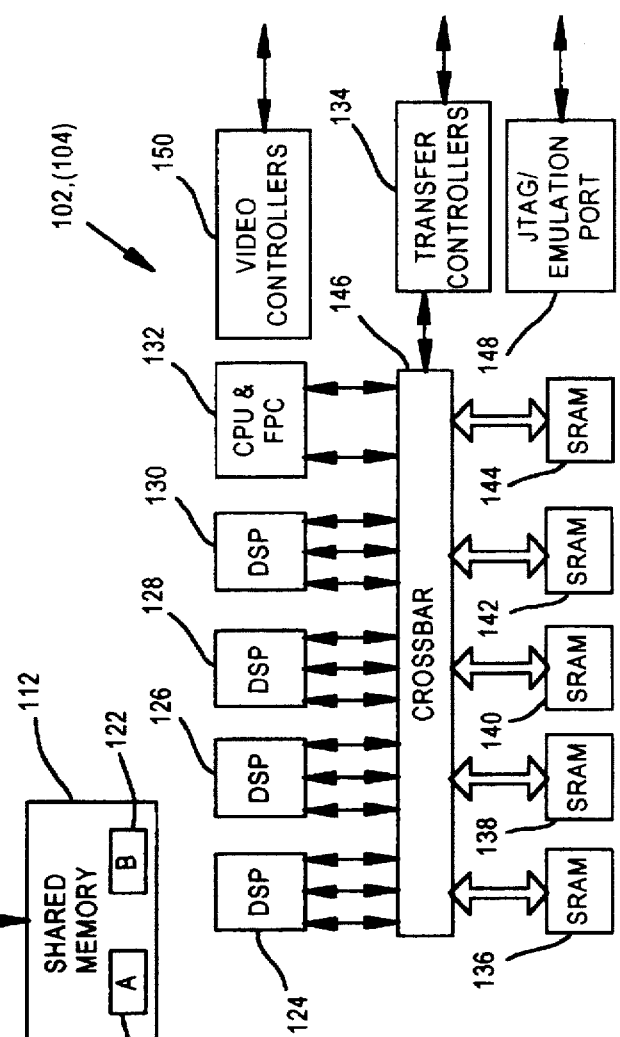
FIG. 4 is a block diagram for one embodiment of a multiprocessor of FIG. 4.

In one embodiment each processor 102, 104 includes one or more digital signal processors. In a specific embodiment each processor 102, 104 is a multiprocessor, such as a Texas Instruments multimedia video processor ("MVP") (part no. TMS320C80). FIG. 4 shows a block diagram of an MVP multiprocessor. The MVP combines on a single semiconductor chip, four fully programmable digital signal processors 124, 126, 128, 130 and a master processor 132 for handling multiple data streams via a transfer controller 134. Several on-chip random access memory (RAM) devices 136, 138, 140, 142, 144 serve as resident memory accessible to the digital signal processors (DSPs) 124-130 via a crossbar network 146. The MVP has a throughput rating of approximately 2 billion operations per second. The master processor 132 is a RISC processor with an integral floating point unit. According to this embodiment the master processor 132 coordinates and distributes processing tasks among the DSPs 124-130 and manages external off-chip communications. A JTAG/emulation port 148 is included for aid in testing, development and diagnostics.

Each DSP 124-130 includes two address generators, three input 32-bit ALUs, a 16×16 multiplier, three zero-overhead loop controllers, and a 32-bit barrel shifter. Each RAM 136-144 has a 10 kB capacity providing 50 kB of single-cycle SRAM. Memory 136-144 is partitioned in blocks with each block serving as either data RAM, parameter RAM, data cache or instruction cache. The data caches and instruction caches serve as a primary cache. The transfer controller 134 services the on-chip caches and interfaces to external memory (e.g., local memory 106 or 108, and shared memory 112).

The MVP also includes a pair of video controllers 150. Controllers 150 generate video synchronization signals or synchronize data transfer rates with external video signals.

Referring again to FIG. 3, each multiprocessor 102, 104 has a respective dedicated local memory 106, 108, serving as a secondary cache. Each local memory 106, 108 has capacity for storing a frame of ultrasound data. In one embodiment a 2 MB capacity is provided at each local memory 106, 108. In addition shared memory 112 is included. In one embodiment shared memory 112 is implemented as two separate 64 MB memory banks 120, 122 for a total of 128 MB shared memory. The storage capacity of local memory 106, 108 and shared memory 112 varies for alternative embodiments. The multiprocessors 102, 104 access shared memory through crossbar switch 110. For a two multiprocessor embodiment, a 2×2 crossbar switch is implemented. The purpose of the crossbar switch 110 is to allow the multiple processors 102, 104 simultaneous access to the shared memory banks. The crossbar switch 110 includes a pair of transceivers for each input channel, along with a crossbar controller.

The function of the crossbar controller is (i) to manage requests for access and (ii) to refresh shared memory 112. If a multiprocessor 102 requests access to a shared memory bank 120, 122 not currently being accessed by the other multiprocessor 104, then the access is granted. If the multiprocessor 102 requests access to a shared memory bank 120, 122 currently being accessed, then the multiprocessor 102 waits until the memory bank is available. Simultaneous access to a shared memory bank 120, 122 thus is available when the accesses are to separate memory banks. For reconciling simultaneous requests for access, one multiprocessor 102 is prescribed to have priority for a specific one shared memory bank 120, while the other multiprocessor 104 is prescribed priority for the other shared memory bank 122. If both multiprocessors 102, 104 request access to a common bank, then the processor with the prescribed priority for that bank is granted access. However, to avoid lengthy delays, the other multiprocessor is granted access after the current access, even if the higher priority multiprocessor comes right back with a second request. For example, consider the case in which multiprocessor 102 has the prescribed priority to the first memory bank 120. The first multiprocessor 102 makes two sequential requests for access to bank 120, while multiprocessor 104 also makes a request to bank 120. Because of the prescribed priority, the first multiprocessor 102 is granted access for its first request. Next, however, the second multiprocessor 104 is granted access. Then, the first multiprocessor 102 is granted access for its second request.

System control signals are received by apparatus 70 from the system controller 14 via an interface 114. The frame buffer/controller 116 serves as a data interface with the ultrasound front end (e.g., beamformer 20), the back-end processing subsystem 30, or another subsystem 30. The output buffer/controller 118 serves as a data interface between the apparatus 70 and the back-end processing subsystem 30 or another subsystem 30, and/or one or more output devices.

Method Overview

The method for automatically measuring fetal head size eliminates the need for the operator to estimate curve shapes and distances. Instead the operator need merely capture a 2D image of a target object (e.g., the fetal head) at a desired orientation and set a marker at an approximate midpoint of the displayed image of the object. According to one embodiment of the invention, a filtered gradient of the image serves as a data sample set from which fetal head measurements are derived.

An initial boundary of a fetal head is estimated automatically using filtering techniques such as statistical filtering. The initial boundary is contracted and improved to derive an inner boundary estimate of the fetal skull using an active contour model. Thereafter, the inner boundary is expanded. The active contour model then is applied to the expanded boundary to derive the outer boundary estimate. Fetal head size then is automatically computed from the inner and outer boundaries of the fetal head. Following is a description of the active contour model used by the present invention and sections on specific embodiments for various steps of the inventive method.

Active Contour Model

The present invention uses an active contour model for finding inner and outer boundaries of the fetal skull. In applying such a model, the boundaries of the fetal head are represented as smooth, unbroken boundaries that lie along high gradient points (e.g., edges) in the fetal head image. For example, the contour passing over an image of the fetal head may be represented by $v(s)=(x(s),y(s))$, where x and y are the coordinates of the contour on the fetal head image, and s is a normalized contour length which defines parameters of the contour.

To select the contour from the image points an internal energy term and external energy term are defined. Each possible configuration of the contour (i.e., fetal head boundary) has an associated energy which is a combination of internal energy and external energy. Features of interest on the image are detected by defining the internal energies and external energies of the contour so that the desired contour has the lowest energy. The internal energy is defined to keep the contour smooth. The external energy is defined to attract the contour toward the boundary of the object being imaged. The internal energy, $E_{int}$, is a weighted measure of contour length and curvature:

$$E_{int}=\int_0^1(\alpha\|v_s(s)\|^2+\beta\|v_{ss}(s)\|^2)ds$$

where $v_s(s)$ is the first derivative of $v(s)$;

$v_{ss}(s)$ is the second derivative of $v(s)$; and $\alpha$ and $\beta$ are fixed weights for points on the contour.

The external energy term attracts the contour to desired features. The desired features for a fetal head image are the fetal head boundaries or edges. These edges have high gradient values. The external energy, $E_{ext}$, is as follows:

$$E_{ext}=-\int_0^1\{\gamma G_\sigma*\|\nabla I(v(s))\|\}ds$$

where $\nabla I$ is the 2D gradient of the image intensity, I;

$G_\sigma$ is a 2D gaussian function with a standard deviation, $\sigma$;

* is a convolution operator; and $\gamma$ is a fixed weighting factor for the points on the contour. The external energy also is called the image energy. The derivative of the image energy along respective directions (e.g., x, y) are the image forces. $f_x$ is the image force in an x direction. $f_y$ is the image force in a y direction. The fetal head boundary is estimated from the ultrasound image data by choosing the boundary with the lowest total energy (lowest internal and external energy). Specifically, the optimum contour representing the fetal head boundary is found by minimizing the following cost function:

$$E(v)=\int_0^1\{\gamma d(v,\nabla I)+\alpha\|v_s\|^2+\beta\|v_{ss}\|^2\}ds.$$

Here, I is the input fetal head image; $\nabla I$ is the gradient of the fetal head image I; $d(v,\nabla I)$ is a function that computes the extent to which the contour, v, passes through the "edges", or points of high gradient, in the fetal head image I; and $v_s$ and $v_{ss}$ are the first and second derivatives of the contour v with respect to the parameter s. The model parameters α, β, and γ control the relative importance of the three terms in finding the optimal contour on the fetal head image. Higher values of α and β encourage shorter and smoother contours, respectively, while higher values of γ encourage more irregular contours which follow edges of the fetal skull more closely. The model parameters α, β, and γ are predetermined off-line for a given implementation (e.g., one set for a fetal head measurement; another set for measurement of a different object's boundary). This cost function is minimized by using an iterative gradient descent optimization method. In solving the cost function an initial point within the boundary is provided by the operator. Alternatively, the operator need not select an initial point. Instead, an initial point is prescribed to be a midpoint of the display image. In addition, it is known that the boundary is a closed curve.

Deriving an Initial Fetal Head Boundary

Figure 5:
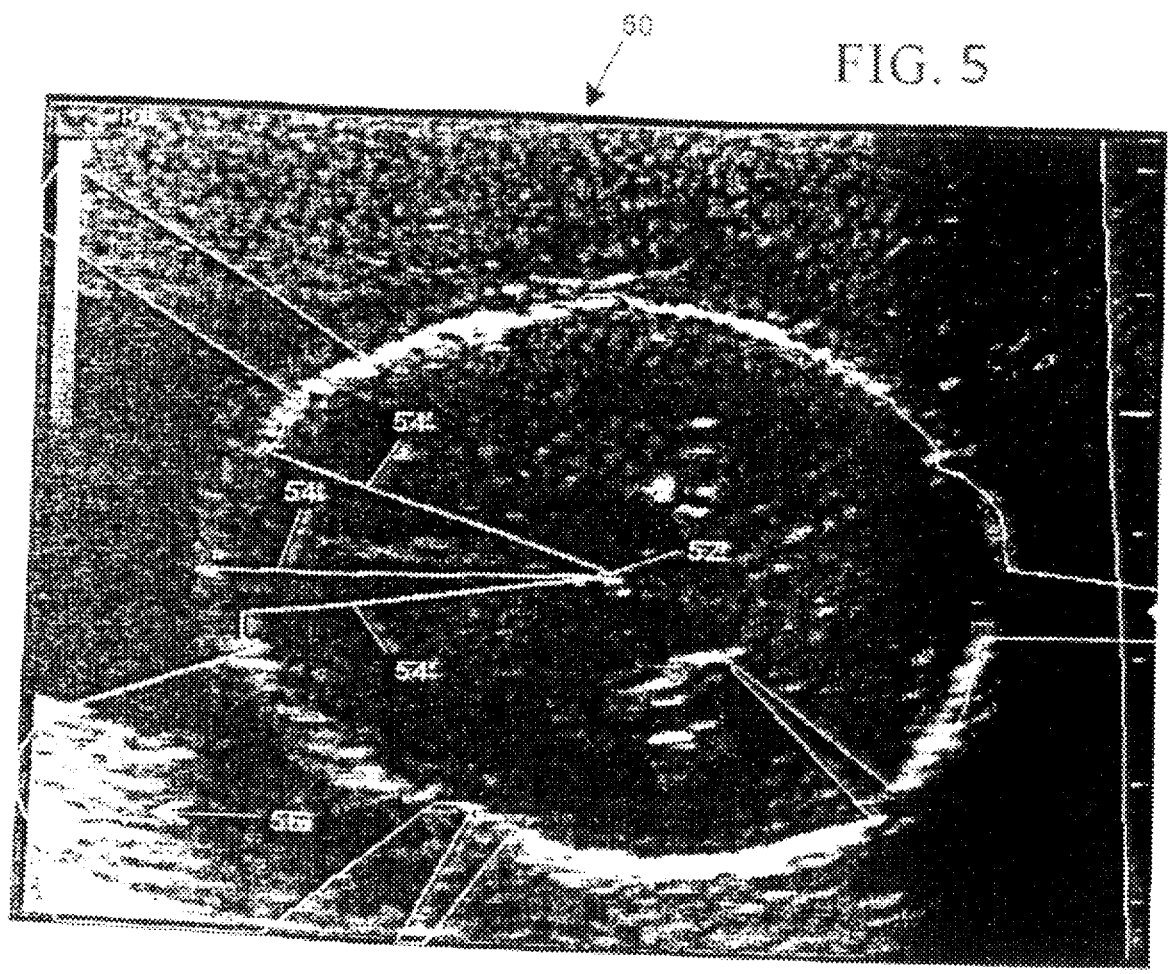
FIG. 5 is an ultrasound display image of a fetal head with overlaid scan lines at a first step of a fetal head measurement method according to one embodiment of the invention.

To apply the active contour model, first an initial contour on the fetal head image is chosen. Accordingly, the method of the present invention begins with a step of detecting a rough initial boundary of the fetal skull. Preferably, the initial contour is close to the displayed boundary of the fetal head. FIG. 5 shows a fetal head boundary detected in the first step in the method according to a preferred embodiment of the invention.

To detect the initial fetal skull boundary, the user locates a fetal head 50, using ultrasound images. The user positions an ultrasound transducer probe on a mother's abdomen to display the fetus within the womb. The operator manipulates the probe to image fetal head 50 at a desired orientation. Specifically, the probe is preferably oriented to capture a cross-section of fetal head 50 along a longitudinal axis (e.g., from the top of fetal head 50 downward.) The cross-section is captured as a snap-shot and is displayed as a two dimensional ("2D") ultrasound image on a display device such as a CRT. The operator then sets a marker at an initial point 52 that is near the approximate center of fetal head 50. Initial point 52 need not be marked exactly at the center of fetal head 50. Instead, according to the present invention, initial point 52 can be marked within a circle having a diameter of approximately 10 mm, and preferably a diameter of approximately 8 mm, from the true center of fetal head 50 without significant degradation of the resultant fetal head size. (In alternative embodiments, the initial point is automatically taken to be the center of the display image). For subsequent frames of data, the same initial point 52 is used.

According to the present invention, the above steps of detecting fetal head 50 and marking initial point 52 are the only operator actions taken in measuring fetal head size. No further operator actions are necessary for the present invention to automatically measure fetal head size. However, further operator interaction may be desired to incorporate prior information known by the user about fetal head size parameters. These desired operator interventions can further refine the automatic measurements of fetal head size made according to the present invention.

After the user detects fetal head 50 and marks initial point 52, the present invention automatically takes radial samples of a filtered gradient of the image of fetal head 50. Here, the image is preferably filtered by the derivative of a Gaussian gradient of the input image. According to the invention, the radial samples are taken to define radial maxima points. The radial samples are taken along radial lines 54 that extend outward from initial point 52 to maxima points (i.e., the points along radial lines 54 corresponding to a maximum ultrasound echo strength or image brightness). In one embodiment, the radial samples are the image gray values underlying the points that are one pixel distance apart from one another on the radial lines. The present invention determines the point of maximum gray value, representing the strongest edge, on each radial line 54. These maxima define a crude boundary of fetal head 50. The present invention may generate more than 100 radial lines 54, and preferably generates approximately 120 radial lines 54; when approximately 120 radial lines 54 are drawn, each radial line 54 is spaced approximately 3 degrees apart. To reduce the computational complexity in some embodiments a zone of exclusion represented by a circle is used. Points lying within the circle are not considered. Such circle is prescribed to be less than a typical fetal head minimum diameter for a given image size.

Some points along the true fetal skull may not have been captured during the ultrasound scan. Therefore, some of the radial maxima points may occur at an exaggerated radial increment beyond the true fetal skull. These points not lying on the true boundary of fetal head 50 are referred to herein as outlier points 56. As seen in FIG. 5, the crude boundary of fetal head 50 may include a number of outlier points 56. It is therefore desirable to remove outlier points 56 from the crude boundary.

Removing Outlier Points

Figure 6:
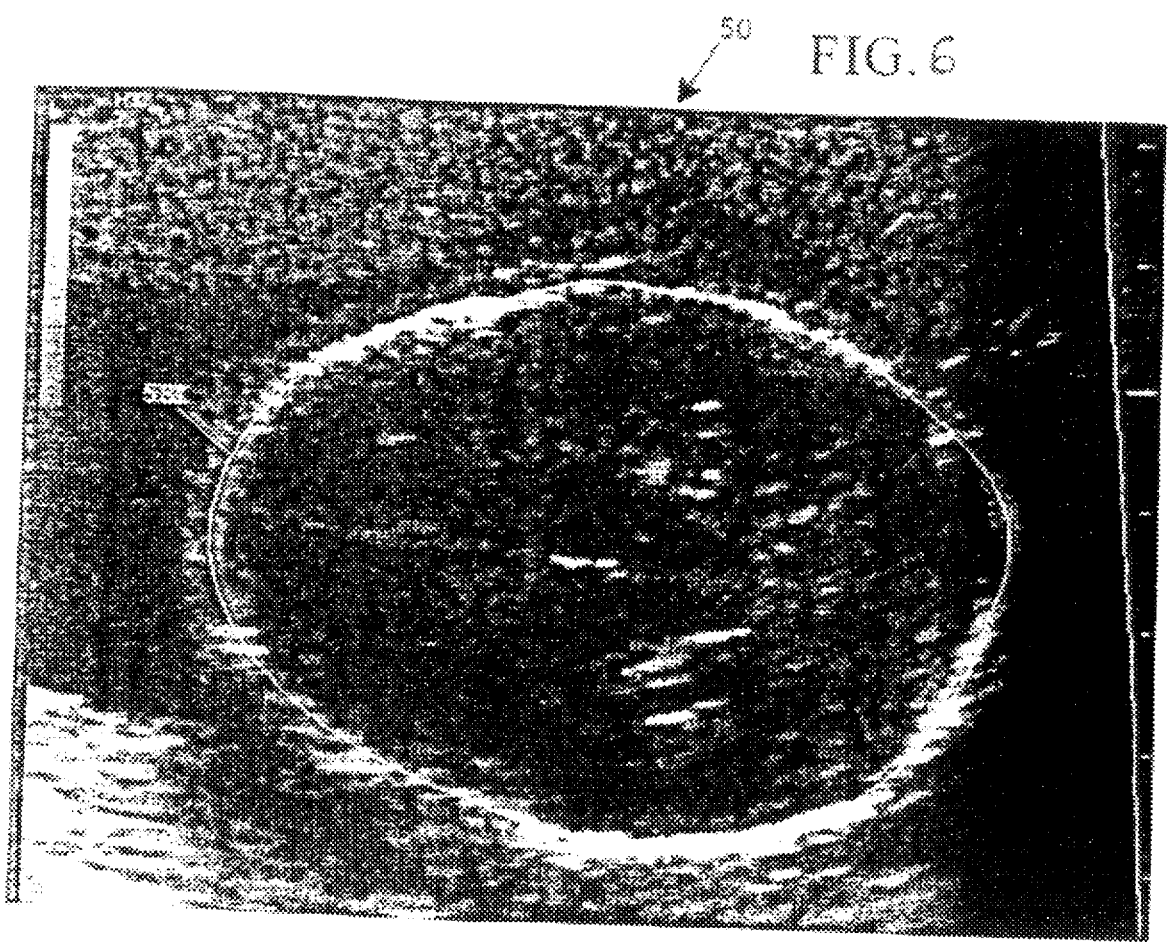
FIG. 6 is an ultrasound display image of a fetal head with an overlaid crude initial boundary at another step of a fetal head measurement method according to one embodiment of the invention.

FIG. 6 shows the next step in the preferred method of the present invention in which the crude boundary of fetal head 50 is filtered to remove outlier points 56. The present invention automatically applies a statistical filter to the crude boundary. The statistical filter removes boundary points with a radial distance more than a predetermined deviation from the mean radius from initial point 52. The amount of deviation represents a tradeoff between how close initial point 52 must be marked to the center of fetal head 50 and the accuracy of the fetal head size measurements. For example, in one embodiment, the predetermined deviation is two standard deviations from the mean radius from initial point 52. A predetermined deviation of two standard deviations permits the user to select the initial point 52 close to the center of fetal head 50, as described above. A larger deviation, such as, for example, three standard deviations, permits an even greater flexibility in selecting initial point 52. However, the accuracy of fetal head size measurement may decrease. Conversely, a smaller deviation, such as one standard deviation, results in a more accurate determination of fetal head size. However, initial point 52 must be marked closer to the center of fetal head 50 than if two standard deviations are used.

In one embodiment the statistical filter is applied to derive the initial boundary 58. In an alternative embodiment a symmetric filter also is applied for removing all points on the boundary that are not substantially symmetric to each other with respect to initial point 52. The degree of symmetry represents a tradeoff between how close initial point 52 must be marked to the center of fetal head 50 and the accuracy of the fetal head size measurements. In one embodiment, the margin of error in the symmetrical filter is 5 mm. A larger margin of error in degree of symmetry, such as 10 mm, permits the user to select initial point 52 close to the center of fetal head 50, as described above. However, the accuracy of fetal head size measurement may decrease. Conversely, a smaller margin of error in degree of symmetry, such as 2 mm, results in a more accurate determination of fetal head size. However, initial point 52 must be marked closer to the center of fetal head 50.

After the filtering step or steps, there is an initial boundary 58 as shown in FIG. 6. Preferably, the initial point 52 is saved and used as the initial point for deriving a new initial boundary 58 for subsequent frames of image data.

Deriving Inner and Outer Boundaries

Figure 7:
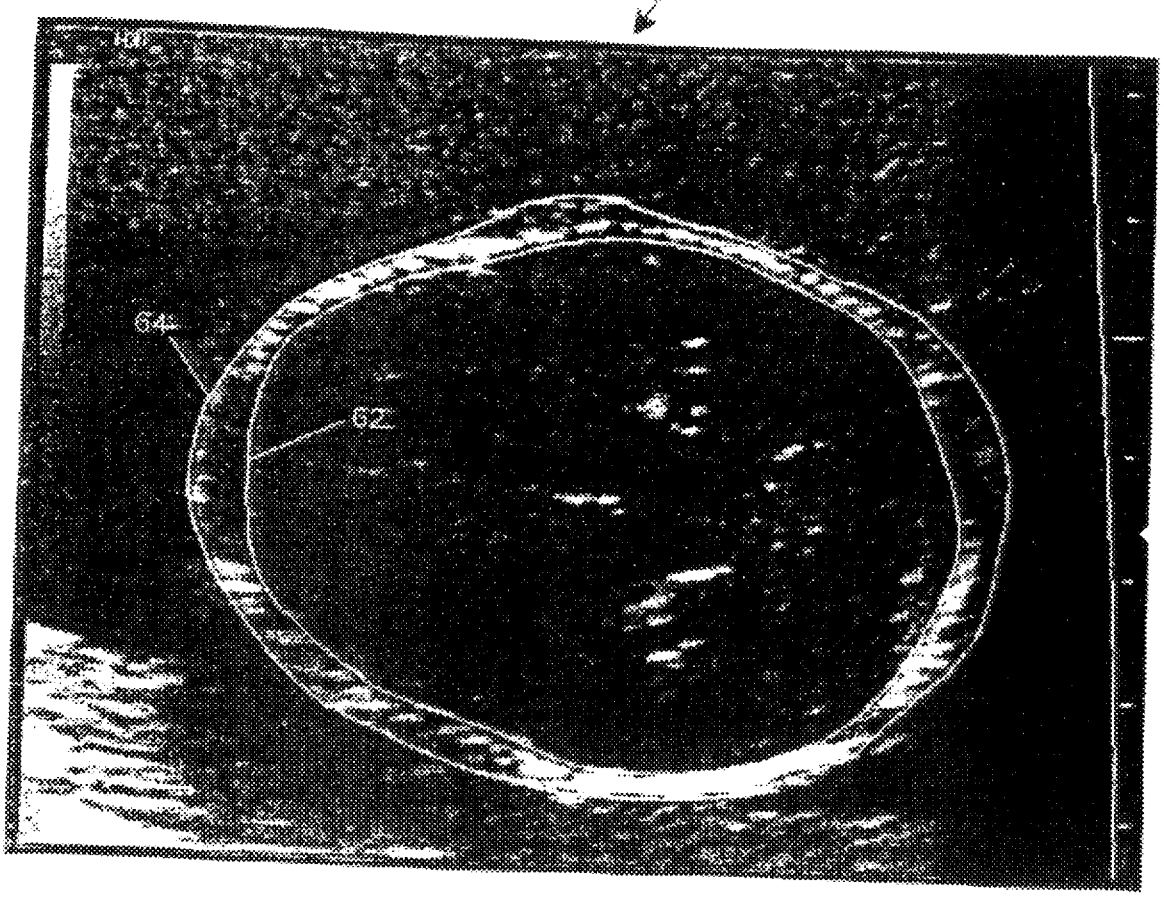
FIG. 7 is an ultrasound display image of a fetal head with overlaid inner and outer fetal head boundaries at another step of a fetal head measurement method according to one embodiment of the invention.

FIG. 7 shows the next step in the preferred method of the present invention in which the initial boundary 58 is adjusted to derive a first boundary of the inner and outer boundaries of the fetal skull. In one embodiment the initial boundary 58 is contracted by a standard fetal skull thickness. Standard fetal skull thickness can vary between 1–3 mm. In one embodiment of the invention, a standard fetal skull thickness of approximately 1.2 mm is used.

The active contour model is applied to the contracted curve to derive the inner boundary 62. The image I used for this first pass of the active contour model is the original image of fetal head 50 filtered with the derivative of a Gaussian with a small standard deviation. The standard deviation is of a size to prevent the inner and outer edges of fetal head 50 from appearing as a merged boundary during the modelling process.

The active contour model parameters $\alpha$, $\beta$, and $\gamma$ are predetermined off-line and fixed for a given implementation. For example, the parameters are fixed for performing fetal head measurements. A different set of parameter values are used for a different implementation (e.g., measure boundary of a different object). The contouring process is an iterative process of fitting the contracted curve and ultrasound image data I to the active contour model. In a preferred embodiment the number of iterations is preassigned. In an alternative embodiment, once the iterations achieve less than a threshold improvement over a prior iteration (e.g., when the model parameters $\alpha$, $\beta$, and $\gamma$ and inner boundary 62 stop changing), the iterative process stops. In one embodiment, the iterative process stops when there is less than an average of 1 pixel improvement for 10 consecutive iterations.

To derive the outer boundary 64, the inner boundary 62 is expanded by applying an expansion factor, (e.g., a standard fetal skull thickness). The active contour model then is applied to the expanded boundary. In a preferred embodiment, the number of iterations is preassigned. In an alternative embodiment the iterations cease when the model parameters $\alpha$, $\beta$, and $\gamma$ and the outer boundary 64 stop changing. As seen in FIG. 7, the results of this stage of processing are inner and outer boundaries 62 and 64 of fetal head 50.

In an alternative embodiment the outer boundary is derived first, then the inner boundary is derived from an outer boundary. In another embodiment, a modified curve is derived from the initial boundary using a first pass of the active contour model. In deriving the modified curve a larger standard deviation is used. The image I used for this first pass of the active contour model is the original image of fetal head 50 filtered with the derivative of a Gaussian with a large standard deviation. This large standard deviation ensures that the contour is attracted to the edges from large distances. However, it merges the inner and outer boundaries of fetal head 50. Therefore, the modified boundary does not pass through either the inner boundary or the outer boundary of fetal head 50. Instead, the modified boundary passes through the fetal skull between the inner and outer boundaries of fetal head 50. The inner and outer boundaries then are derived from the modified boundary using second passes of the active contour model.

Measuring Head Circumference and Biparietal Diameter

Figure 8:
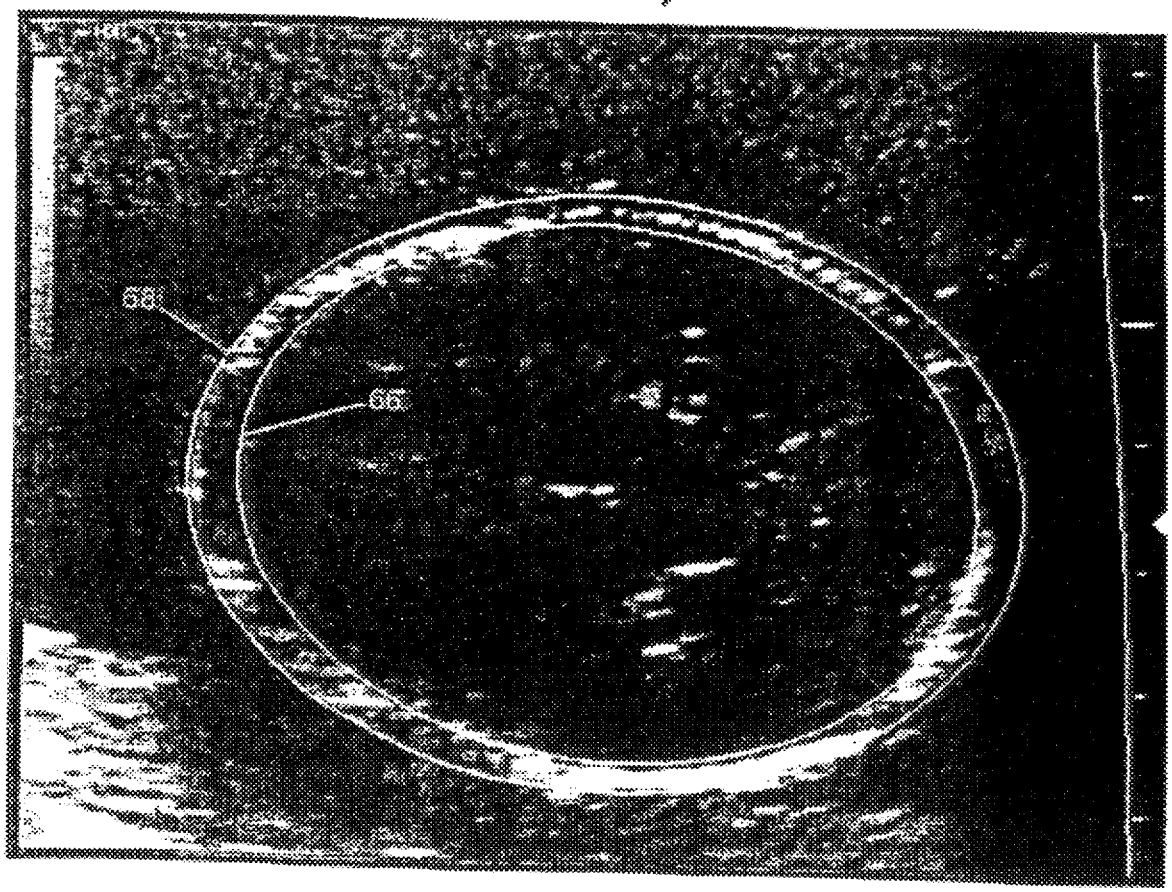
FIG. 8 is an ultrasound display image of a fetal head with overlaid inner and outer ellipses fitted to the inner and outer fetal head boundaries at another step of a fetal head measurement method according to one embodiment of the invention.
Figure 9:
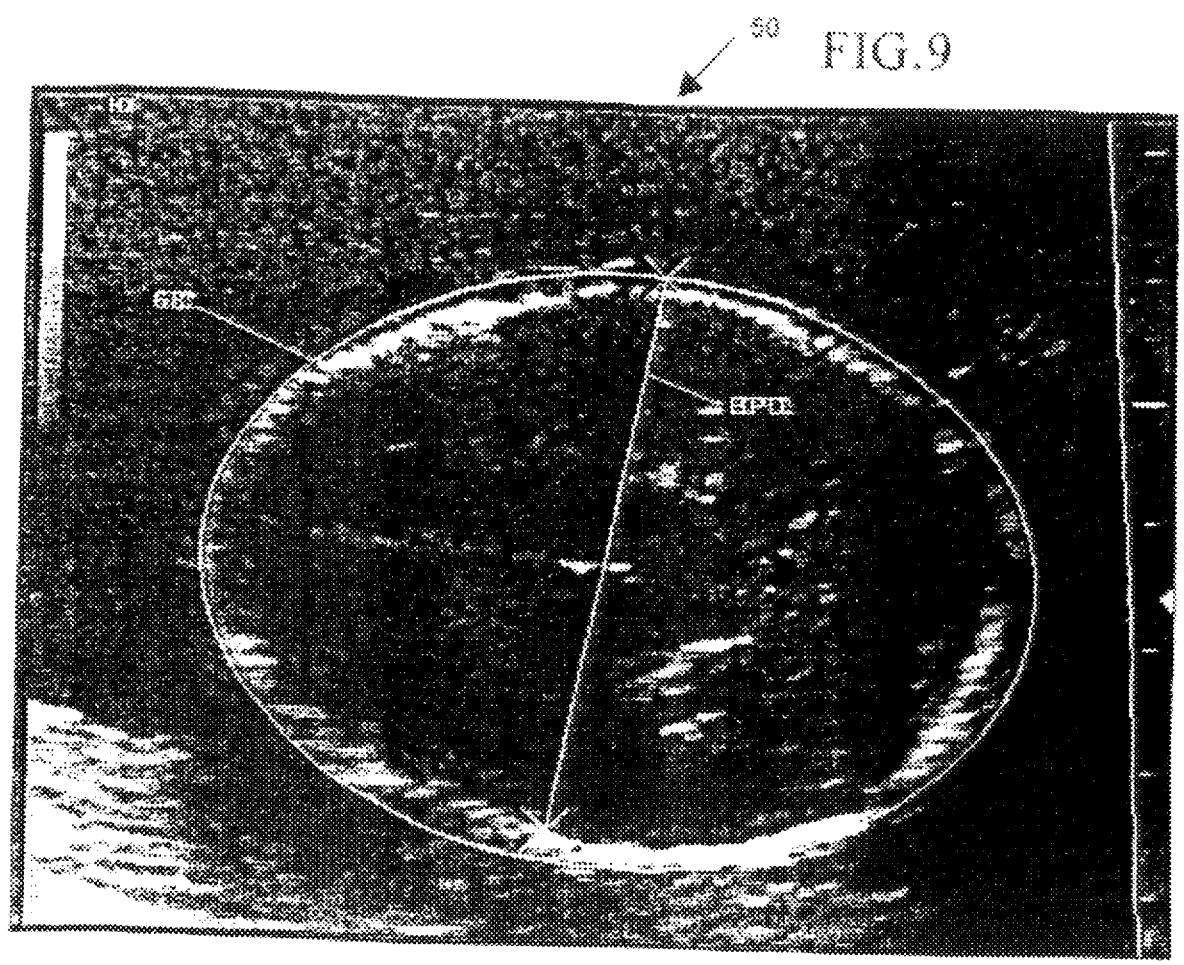
FIG. 9 is an ultrasound display image of a fetal head with overlaid lines indicating head circumference and biparietal diameter.

FIGS. 8 and 9 show the final steps of the method of the preferred embodiment of the present invention in which fetal head size is automatically derived from inner boundary 62 and outer boundary 64. As shown in FIG. 8, inner and outer ellipses 66 and 68 are fit to inner and outer boundaries 62 and 64, respectively. As shown in FIG. 9, head circumference HC for fetal head 50 is the circumference of outer ellipse 68. The circumference HC of outer ellipse 68 is calculated by solving the following equation:

$$HC = 4a \int_{t=0}^{\pi/2} \sqrt{1 - e^2 \sin^2 t} \; dt,$$

where a=distance from the center of fetal head 50 to a major vertex of the major axis of outer ellipse 68;

c=distance from the center of fetal head 50 to a focus of outer ellipse 68; and e=c/a, the eccentricity of outer ellipse 68.

Biparietal diameter BPD, also shown in FIG. 9, is the average length of the minor axes of inner ellipse 66 and outer ellipse 68.

Fetal Head Processing Allocation Among Multiple Processors

Figure 10:
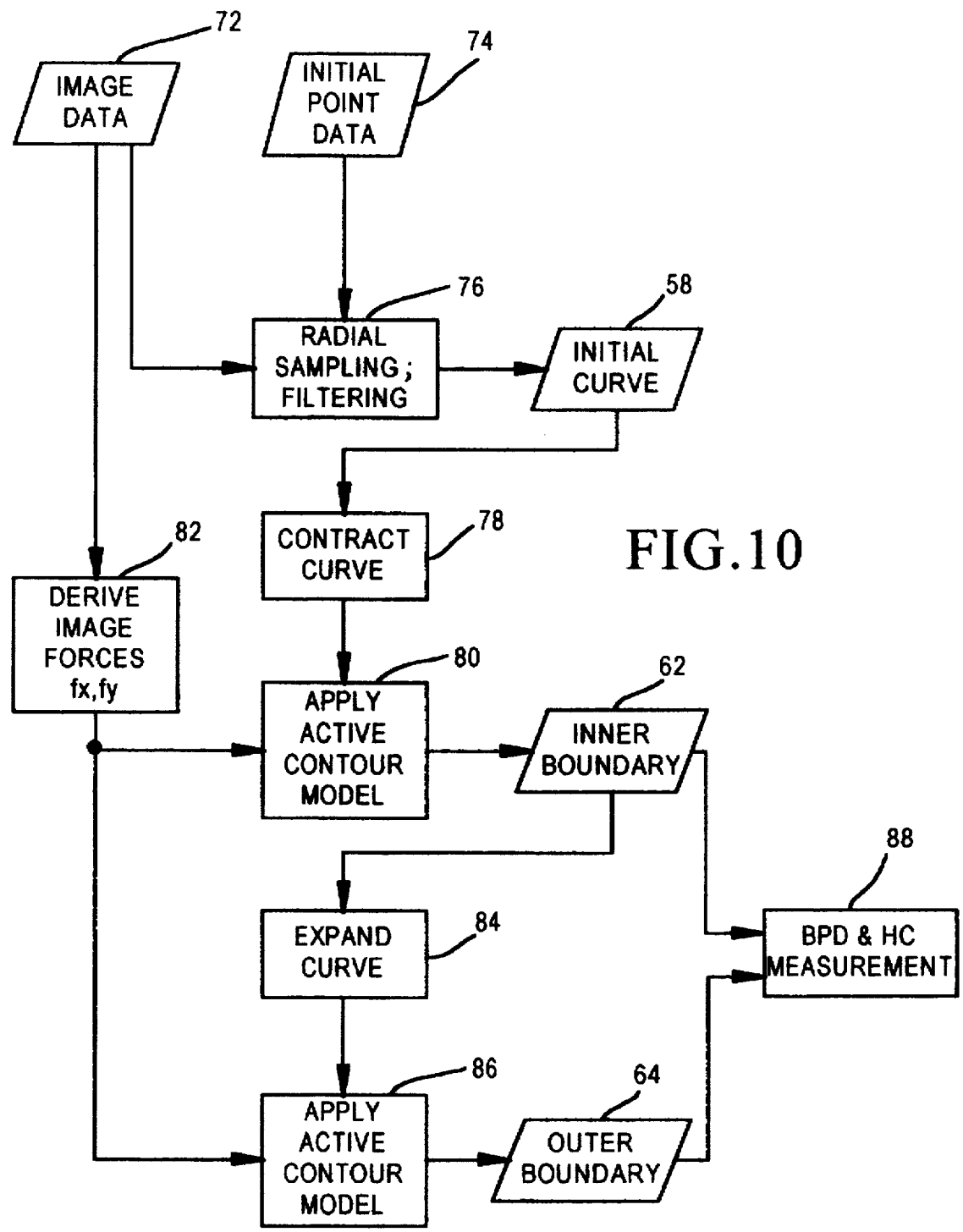
FIG. 10 is a flow chart of an embodiment of the fetal head measurement process of this invention.

FIG. 10 is a flow chart showing a preferred embodiment of the fetal head measurement process. Image data 72 and initial point data 74 are inputs to the process. The image data corresponds to a frame of image data. The initial point corresponds to the marker point selected by the operator (or prescribed by the system). As step 76 radial sampling and outlier filtering are performed to obtain initial curve 58. In the depicted embodiment, the initial curve is contracted at step 78. In an alternative embodiment the initial curve is derived only for a first image frame. For subsequent image frames, the final curve (e.g., inner boundary; outer boundary) from a prior frame is used as the initial curve 58 or the contracted curve.

At step 80 the active contour model is applied to the contracted curve to derive the inner boundary 62. At step 84 the inner boundary 62 is expanded. At step 86 the active contour model then is applied to the expanded curve to derive the outer boundary 64. The inner and outer boundaries 62, 64 then are used at step 88 to perform the fetal head size measurements, BPD and HC. Before the active contour models is applied at each of steps 80 and 86, image forces, $f_x$ and $f_y$ are derived at step 82. These image forces are used by the active contour model to efficiently derive the inner and outer boundaries 62, 64.

Image force are computed as the derivative of the image energy. The image energy is computed by convolving a gaussian, $G_\sigma$, with the gradient image, $|\nabla I|$. Because such computation is commutative and takes a lot of processing time, instead of convolving a gaussian with a gradient image, the derivative of the gaussian is convolved with the image.

$$G_\sigma * \|\nabla I\| = \|\nabla G_\sigma * I\|$$

This rearrangement reduces computation complexity. The time to perform a gradient operation is reduced by precomputing the derivative of the gaussian. The equation of a 2D circular gaussian with a standard deviation of $\sigma$ is of the form: A exp$[-(x^2+y^2)/2\sigma^2]$. The derivative of the gaussian along the x and y directions is of the form: $(-Ax/\sigma^2)$exp$[-(x^2+y^2)/2\sigma^2]$ and $(-Ay/\sigma^2)$exp$[-(x^2+y^2)/2\sigma^2]$, respectively. The number of computer operations in a 2D process is on the order of $O(p^2N^2)$ where N×N is the size of the image and p×p is the size of a kernel. To reduce the computational complexity, each of these 2D gaussian derivative kernels is separated into two 1D kernels, as follows:

$$\frac{-Ax}{\sigma^2} \exp\frac{-(x^2+y^2)}{2\sigma^2} = Bx\exp\frac{-x^2}{2\sigma^2} \times C\exp\frac{-y^2}{2\sigma^2},$$

$$\frac{-Ay}{\sigma^2} \exp\frac{-(x^2+y^2)}{2\sigma^2} = By\exp\frac{-x^2}{2\sigma^2} \times C\exp\frac{-y^2}{2\sigma^2}$$

where $A/\sigma^2 = B \times C$. As a result, the number of operations in generating one gradient image is on the order of $O(2pN^2)$. In one embodiment a kernel size (p) of 13 is used to approximate a gaussian function with a standard deviation ($\sigma$) of 3. Separating the kernel reduces the number of required multiplications and additions by a factor of p/2 (e.g., 6.5 for p=13). The 1D kernel equations are very similar. So rather than creating a separate y-direction kernel, a convolution in the y direction is performed by rotating the input image 90 degrees and using the same kernels used for convolution along the x direction. The two kernels used for convolving the derivative of the gaussian with the image are:

Kernel 1: $Bx\exp\frac{-x^2}{2\sigma^2}$, and

Kernel 2: $C\exp\frac{-x^2}{2\sigma^2}$

Figure 11:
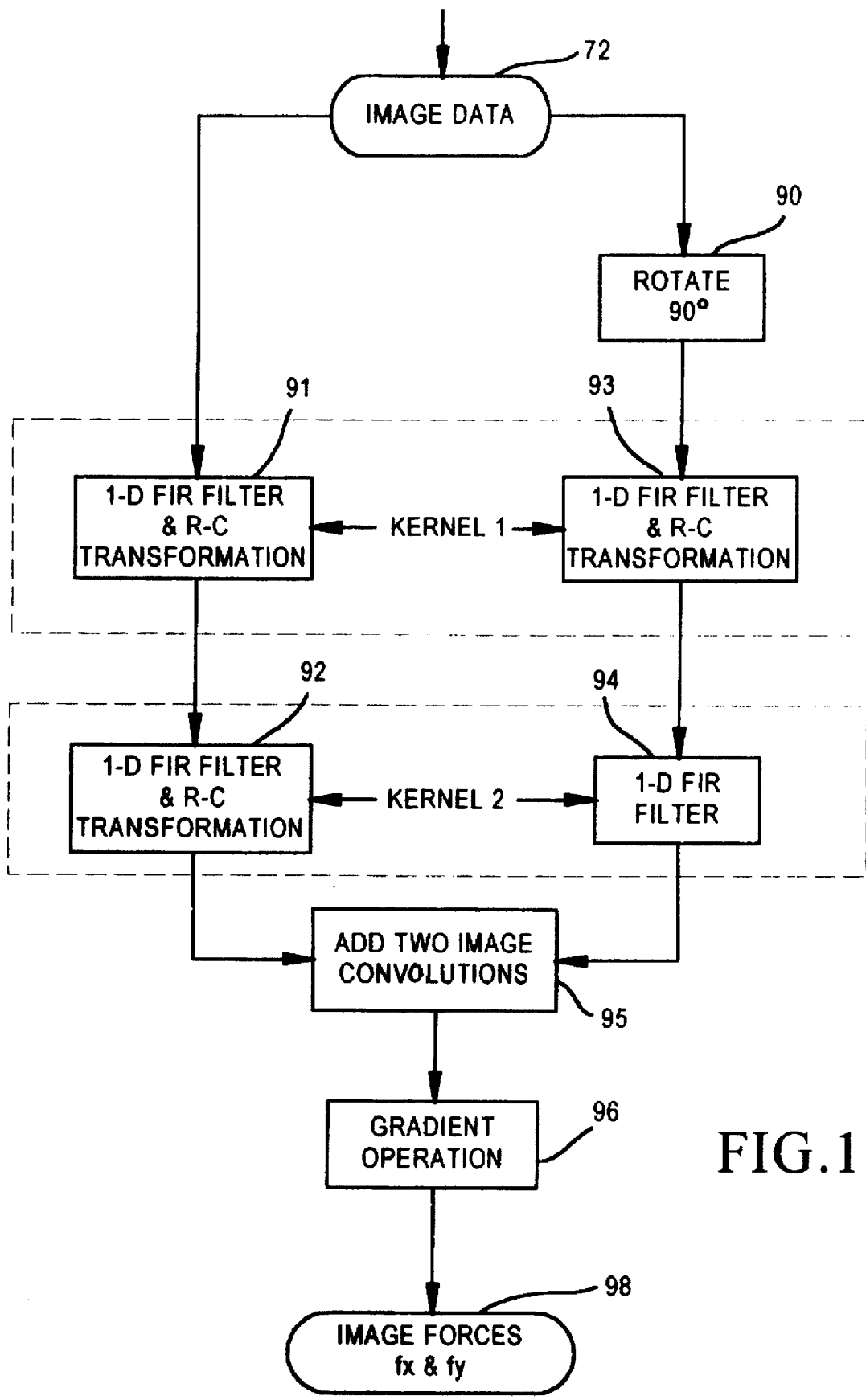
FIG. 11 is a flow chart of the image force derivations steps.

FIG. 11 shows the flow chart for deriving the image forces. At step 72, the image data is received. There are two convolutions performed on the image data. For one convolution, at step 91 the image data is passed through a 1D finite impulse response filter and row-column (R-C) transformation using Kernel 1. The row-column transformation reorganizes rows of image data into columns to cause a 90 degree image rotation. At step 92 the result is passed through another 1D finite impulse response filter and row-column transformation using Kernel 2. For the other convolution the image data is first rotated 90 degrees at step 90. The rotated image data then is through a 1D finite impulse response filter and row-column transformation using Kernel 1 at step 93. At step 94 the result is passed through another 1D finite impulse response filter and row-column transformation using Kernel 2. The results of the two convolutions are added at step 95 to produce the image energy for the input image. The image forces then are derived by taking the derivative of the image energy in x and y directions. This is performed as a gradient operation at step 96. The result is image forces $f_x$ and $f_y$ at step 98.

When applying the active contour model, the image forces deform the x and y coordinates of the curve. Smoothness and continuity constraints are then imposed on the deformed curve. In performing the processing, 16-bit fixed point representations are used in place of floating point numbers to further decrease computation time.

Figure 12:
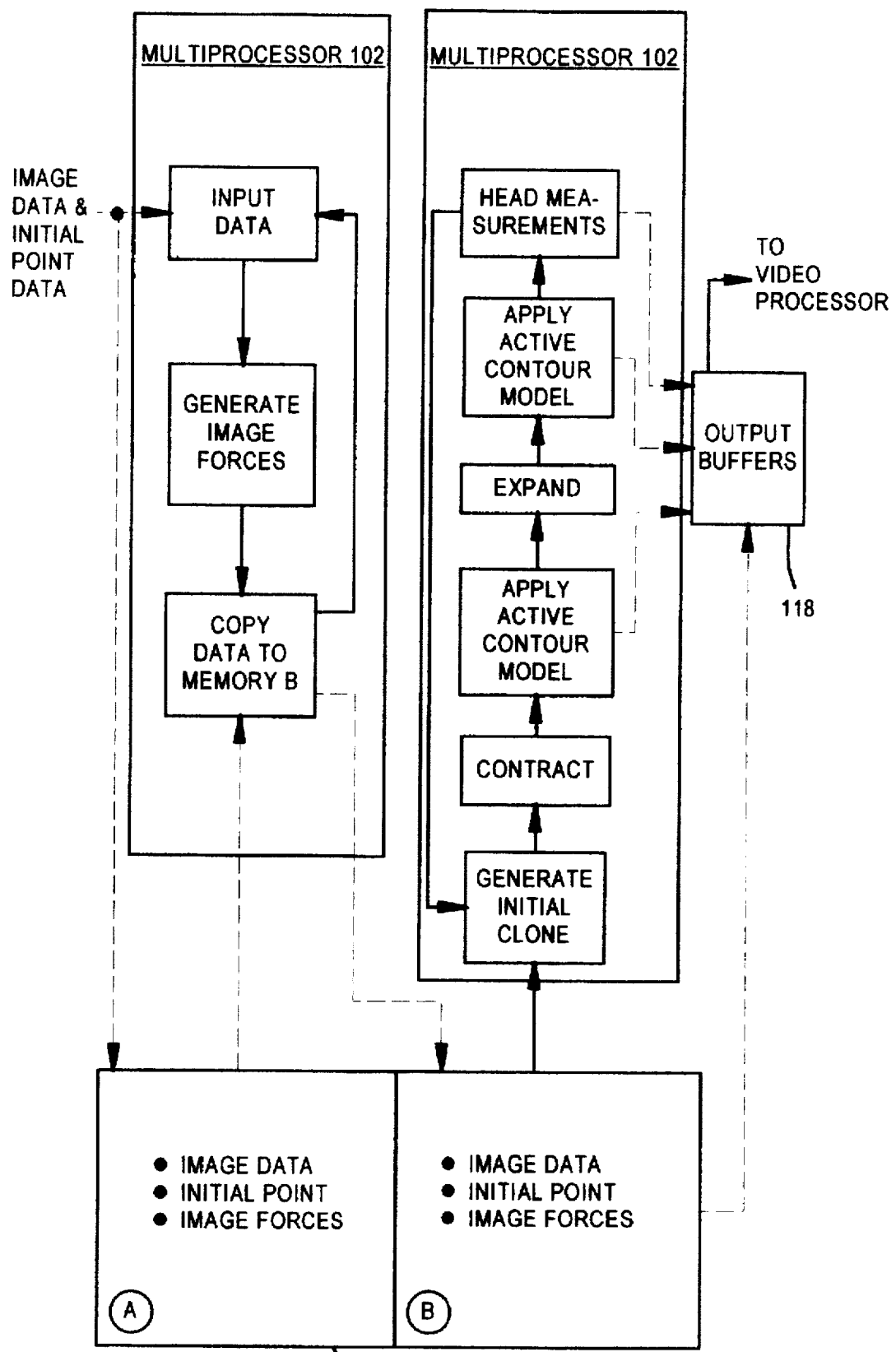
FIG. 12 is a diagram of the task allocation among the multiprocessors of FIG. 3.

FIG. 12 shows the task division among the multiprocessors 102, 104. Referring to FIG. 4 each multiprocessor 102, 104 includes four digital signal processors 124, 126, 128, 130 in a parallel architecture. The image data is divided into 4 equally sized row-slices. One row slice is assigned to each processor 124, 126, 128, 130 to reduce execution time to a fourth. Two sets of convolutions are carried out row by row using the 13×1 kernels (i.e., Kernel 1 and Kernel 2). The CPU 132 controls the processor 124, 126, 128, 130 by passing parameters. The multiprocessors 102, 104 each include an intelligent transfer controller 134 that transfers data between on-chip and external memory systems independent of the processors 124–130 and CPU 132. In one embodiment one row for each of two image slices is input to the multiprocessor 102 at a time (The row for one image slice is the original image data. The row for the second image slice is the original image data rotated 90 degrees).

For each DSP 124–130 there is a corresponding RAM 136–142. Each one RAM 136–142 is allocated to include three areas for data RAM, another area for parameter RAM and another area for an instruction cache for the corresponding processor 124–130. One data RAM area is allocated as a ping input area. Another data RAM area is allocated as a pong input area. The third data RAM area ia allocated a ping output area and a pong output area. Such mapping reduces the overall execution time by taking advantage of the transfer controller 134's autonomous transfer capability and overlapping the I/O and the processing activities. While a processor 124–130 works on input data stored in the corresponding ping input data area of RAM and stores it in the ping output data area, the transfer controller outputs the prior results from the corresponding pong output data area and loads the next block of data into the corresponding pong input data area of RAM. Also, by allocating the ping and pong output data areas to the third data RAM area, there is less contention for accessing the memory.

The multiprocessors 102, 104 are programmed to perform the measurement process in pipeline fashion. During an n-th cycle the multiprocessor 102 receives an n-th frame of image data and the initial point data via frame buffers 116 (see FIG. 3). The received data is stored in bank A of the shared memory 112. Once the data is input, the multiprocessor 102 then generates the image forces, $f_x$ and $f_y$ based on the processing steps shown in FIG. 11. Once the image forces are derived, the image data, initial point data and images forces are copied into bank B of shared memory 112.

During the (n+1)-th cycle, the multiprocessor 102 receives an (n+1)-th frame of image data via frame buffers 116. The received data is stored in bank A of the shared memory 112. Once the data is input, the multiprocessor 102 then generates the image forces, $f_x$ and $f_y$ for the (n+1)-th frame of image data. Once the image forces are derived, the image data and image forces for the (n+1)-th frame are copied into bank B of shared memory 112.

During the (n+1)-th cycle, the multiprocessor 104 processes the image data from the n-th frame to generate the initial curve, the inner and outer boundaries and the head measurements for such n-th frame of data. The image forces for the n-th stored in memory bank B of shared memory 112 are used to apply the active contour model. Also during the (n+1)-th cycle the multiprocessor 104 outputs the image data, the inner and outer boundaries and the head measurements to the output buffer 118. The outputs data subsequently is moved from the output buffer 118 for video processing and display.

Thus during any cycle, the multiprocessor 102 receives a frame of image data, stores the received data in bank A of the shared memory 112, generates image forces, $f_x$ and $f_y$ for the received frame of data, and copies the image data and image forces for the received frame into bank B of shared memory 112. Concurrently during such cycle, the multiprocessor 104 processes the image data from the received frame of the prior cycle to generate the initial curve, the inner and outer boundaries and the head measurements for such n-th frame of data. In addition the multiprocessor 104 outputs the image data, the inner and outer boundaries and the head measurements to the output buffer 118. In one embodiment the initial point 52, selected by the operator, is stored and used for each frame of data as a seed point for generating the initial boundary at multiprocessor 104. In another embodiment, the inner boundary from a prior frame of data is used as the initial boundary for processing a subsequent frame of image data at multiprocessor 104. The image forces are derived at multiprocessor 102 independent of the initial point 52.

Meritorious Effects and Advantages

One advantage of the method for automatically measuring fetal head size is that the time portion of the diagnostic exam allocated toward fetal head measurement is reduced. A meritorious effect of such time reduction is a decrease in health care costs. Another advantage of the process is reduced inter-observer variability. A meritorious effect of such reduction is more reliable data pool for predicting fetal health, size, and age.

Another advantage of the method of the present invention is that a boundary is detected for a curved object using ultrasound imaging techniques. A meritorious effect of such a boundary detection is that it is not limited to detection of a fetal head boundary. For example, according to the present invention, a boundary is derived from an ultrasound image of a kidney, a liver, a prostate tumor, ventricles of a pediatric brain, or a fetal femur. As a further example, the number and size of ovarian follicles are measured. Moreover, cross sectional area and diameter of arteries and veins are measured from transcutaneous or intravascular ultrasound images. These examples are given as non-limiting examples; a boundary of any curved object can be detected according to the present invention.

Another advantage of the method of the present invention is that a sonographer may be aided in identifying the correct orientation for acquiring a fetal head image. Typically, the fetal head image used for BPD and HC measurements is selected based upon certain landmarks on the image. In addition to identified landmarks, image selection is based upon size of the displayed head. Measurements for the image plane where BPD is the largest are typically chosen as the final measurements among measurements for multiple frames of image data (during which the operator moves the probe to find what the operator perceives to be the best view). Advantageously, the present invention tracks BPD measurement of the fetal head as images change.

According to the present invention, once a fetal head boundary is detected on an image frame, the boundary is used as an initial curve for the next image frame. The sonographer does not need to mark an initial point on every sequential image. This allows the method of the present invention to proceed very quickly and give a sonographer timely feedback regarding transducer orientation.

Although a preferred embodiment of the invention has been illustrated and described, various alternatives, modifications and equivalents may be used. For example, the method can be performed by an image processor internal to a medical ultrasound imaging device, or it can be performed by an external signal processor. Further, the present invention can detect a boundary of a curved object other than a fetal head. Therefore, the foregoing description should not be taken as limiting the scope of the inventions which are defined by the appended claims.

What is claimed is:

1. A method for automatically measuring fetal head size based upon ultrasound image data of the fetal head, the method comprising the steps of:

detecting an ultrasound image of the fetal head;

identifying a radial maxima point on each of a plurality of radii extending from a substantially common vertex point within the fetal head image, each radial maxima point corresponding to an ultrasound sample along its corresponding radius and having a maximum ultrasound echo strength;

defining a first curve from the radial maxima points;

modifying the first curve to define an enclosed initial fetal head boundary;

deriving an inner fetal head boundary and outer fetal head boundary from the initial fetal head boundary and a predetermined fetal skull thickness; and computing fetal head size from the inner fetal head boundary and outer fetal head boundary.

2. The method of claim 1, in which the steps of detecting, identifying, defining, modifying, deriving and computing are repeated for multiple frames of ultrasound image data; and further comprising the step of: selecting computed fetal head size from one of the multiple frames as a final fetal head size.

3. An ultrasound system for automatically measuring fetal head size, the ultrasound system comprising:

a transducer array for transmitting ultrasound energy into a patient in the vicinity of an internal fetus and for receiving echoes of the ultrasound energy, the received echoes being transformed into electronic echo signals;

an image processor for generating ultrasound image data from the received echo signals;

a display device for displaying the ultrasound image data generated by the image processor;

means for identifying a radial maxima point on each of a plurality of radii extending from a substantially common vertex point within a fetal head image, each radial maxima point corresponding to an ultrasound sample along its corresponding radius and having a maximum ultrasound echo strength;

means for defining a first curve from the radial maxima points;

means for modifying the first curve to define an initial fetal head boundary;

means for deriving an inner fetal head boundary and outer fetal head boundary from the initial fetal head boundary and a predetermined fetal skull thickness; and means for computing fetal head size from the inner fetal head boundary and outer fetal head boundary.

4. The system of claim 3, in which the identifying means, defining means, modifying means, deriving means and computing means perform on multiple frames of ultrasound image data; and wherein the computing means selects a computed fetal head size for one of the multiple frames as a final fetal head size.

5. The system of claim 4, wherein the computing means performs in real time and wherein the display device displays computed fetal head size.

6. A method for automatically detecting a curved boundary within an ultrasound image of an object, the image data being formed by scanning the object with an ultrasound transducer to achieve image data, the detected boundary substantially corresponding to a physical boundary of the object, the method comprising the steps of:

testing the image data to identify a plurality of radial maxima points relative to a substantially common vertex point of the object, each of the plurality of radial maxima points being a point along a radial line extending from the vertex point and corresponding to a maximum ultrasound echo strength;

filtering out radial maxima points farther than a threshold distance from the vertex point, the threshold distance being based upon an average distance between the vertex point and the plurality of radial maxima points, wherein the step of filtering points farther than a radial distance results in an initial curve, corresponding to the physical boundary of the object; and modifying the initial curve to derive a first boundary, wherein the step of modifying comprises the step of performing an iterative estimation of the initial curve using an active contour model.

7. A method for automatically detecting a curved boundary within an ultrasound image of an object, the image data being formed by scanning the object with an ultrasound transducer to achieve image data, the detected boundary substantially corresponding to a physical boundary of the object, the method comprising the steps of:

at a first multiprocessor, inputting a frame of the image data and data indicative of a point within the curved boundary of the object;

at the first multiprocessor, generating an image force value for the frame of image data for a first direction and a second direction, where the second direction is orthogonal to the first direction;

at a second multiprocessor, testing image data for a prior frame to identify a plurality of radial maxima points relative to a substantially common vertex point of the object, each of the plurality of radial maxima points being a point along a radial line extending from the vertex point and corresponding to a maximum ultrasound echo strength;

at the second multiprocessor, filtering out radial maxima points farther than a threshold distance from the vertex point, the threshold distance being based upon an average distance between the vertex point and the plurality of radial maxima points, wherein the step of filtering points farther than a radial distance results in an initial curve corresponding to the physical boundary of the object; and at the second multiprocessor, modifying the initial curve to derive a first boundary, wherein the step of modifying the initial curve comprises the step of performing an iterative estimation of the initial curve using an active contour model and image force values for the prior frame of image data derived by the first multiprocessor; and wherein the steps of inputting and generating at the first multiprocessor are performed by the first multiprocessor during an n-th iteration, and wherein the steps of testing, filtering farther, filtering asymmetric, and modifying are performed by the second multiprocessor during the n-th iteration.

8. The method of claim 7, further comprising the step of:

at the second multiprocessor, either one of expanding or contracting the first boundary and modifying the expanded or contracted first boundary to derive a second boundary, wherein the step of modifying the expanded or contracted first boundary, comprises the step of performing an iterative estimation of the expanded or contracted first boundary using the active contour model and image force values for the prior frame of image data derived by the first multiprocessor; and wherein the step of modifying the expanded or contracted first boundary is performed by the second multiprocessor during the n-th iteration.

9. The method of claim 8, wherein the object is a fetal head, and further comprising the step of:

during the n-th iteration at the second multiprocessor, computing fetal head size from the first and second boundaries derived from the image data of the (n−1)-th frame.

10. An ultrasound system for automatically detecting a curved boundary within an ultrasound image of an object, the image data being formed by scanning the object with an ultrasound transducer to achieve image data, the detected boundary substantially corresponding to a physical boundary of the object, comprising a transducer array for transmitting ultrasound energy into a patient in the vicinity of an internal fetus and for receiving echoes of the ultrasound energy, the received echoes being transformed into electronic echo signals;

a sequence of frames of ultrasound image data derived from the received echo signals;

a processing apparatus comprising a first multiprocessor and a second multiprocessor for processing frames of ultrasound image data in pipeline fashion to derive a boundary of the object in the respective frames; and a display device for displaying an ultrasound image of the object and the derived boundary for frames of the ultrasound image data;

wherein for an n-th frame of image data among the sequence of frames, the n-th frame of image data and data indicative of a point within the curved boundary of the object are input to the first multiprocessor, the first multiprocessor generating an image force value for the n-th frame of image data for each a first direction and a second direction, where the second direction is orthogonal to the first direction, wherein while the first multiprocessor inputs the n-th frame of image data and generates the image force values, the second multiprocessor performs a sequence of operations, including (i) testing the image data for an (n−1)-th frame to identify a plurality of radial maxima points relative to a substantially common vertex point of the object, each of the plurality of radial maxima points being a point along a radial line extending from the vertex point and corresponding to a maximum ultrasound echo strength; (ii) filtering out radial maxima points farther than a threshold distance from the vertex point, the threshold distance being based upon an average distance between the vertex point and the plurality of radial maxima points, the filtering resulting in an initial curve corresponding to the physical boundary of the object; and (iii) modifying the initial curve to derive the boundary, wherein modifying the initial curve includes performing an iterative estimation of the initial curve using an active contour model and image force values for (n−1)-th frame of image data derived by the first multiprocessor.

11. The system of claim 10, wherein while the first multiprocessor inputs the n-th frame of image data and generates the image force values, the sequence of operations performed by the second multiprocessor further includes outputting the (n−1)-th frame of image data and the boundary for the (n−1)-th frame.

12. The system of claim 10, wherein while the first multiprocessor inputs the n-th frame of image data and generates the image force values, the sequence of operations performed by the second multiprocessor further includes (iv) either one of expanding or contracting the first boundary and (v) modifying the expanded or contracted first boundary to derive a second boundary, wherein modifying the expanded or contracted first boundary includes performing an iterative estimation of the expanded or contracted first boundary using the active contour model and image force values for the (n−1)-th frame of image data derived by the first multiprocessor.

13. The system of claim 12, wherein the object is a fetal head, and wherein while the first multiprocessor inputs the n-th frame of image data and generates the image force values, the sequence of operations performed by the second multiprocessor further includes computing fetal head size from the first and second boundaries for the image data of the (n−1)-th frame.

14. An ultrasound system for automatically detecting a curved boundary within an ultrasound image of an object, the system comprising:

- an ultrasound transducer which scans the object to achieve image data of the object, the detected boundary substantially corresponding to a physical boundary of the object,
- a processor for processing the image data; and
- a display for displaying an image of the object and the detected boundary;

the processing by the processor comprising:

(i) testing the image data to identify a plurality of radial maxima points relative to a substantially common vertex point of the object, each of the plurality of radial maxima points being a point along a radial line extending from the vertex point and corresponding to a maximum ultrasound echo strength;

(ii) filtering out radial maxima points farther than a threshold distance from the vertex point, the threshold distance being based upon an average distance between the vertex point and the plurality of radial maxima points, wherein the filtering of filtering points farther than a radial distance results in an initial curve, corresponding to the physical boundary of the object; and (iii) modifying the initial curve to derive a first boundary, wherein the modifying comprises performing an iterative estimation of the initial curve using an active contour model, wherein the first boundary is the displayed detected boundary.

* * * * *